United States Patent [19]

Bonnell

[11] Patent Number: 5,056,535
[45] Date of Patent: Oct. 15, 1991

[54] VARUS AND VALGUS LEG MANIPULATOR

[75] Inventor: Leonard Bonnell, Huntingdon Valley, Pa.

[73] Assignee: Leonard Medical, Huntingdon Valley, Pa.

[21] Appl. No.: 467,982

[22] Filed: Jan. 22, 1990

[51] Int. Cl.⁵ .......................... A61F 5/37; A61F 5/04; A61G 13/00
[52] U.S. Cl. .................. 128/882; 128/84 R; 269/328; 606/87
[58] Field of Search .................. 128/882, 84 R, 84 C, 128/165, 166, 87 R, 80 R; 606/87, 88, 97; 269/322, 325, 328

[56] References Cited

U.S. PATENT DOCUMENTS

| | | | |
|---|---|---|---|
| 1,823,248 | 9/1931 | Allison | 269/328 |
| 2,057,992 | 10/1936 | Wiruth | 128/84 R |
| 2,679,445 | 5/1954 | Roehm | 269/328 |
| 2,757,058 | 7/1956 | Broesel | 311/11 |
| 3,066,322 | 12/1962 | Derby | 5/327 |
| 3,318,596 | 5/1967 | Herzog | 269/324 |
| 3,409,287 | 11/1968 | Chervenka | 269/328 |
| 3,833,211 | 9/1974 | Mueller et al. | 269/328 |
| 3,944,205 | 3/1976 | Mueller | 269/166 |
| 4,033,624 | 7/1977 | Jun | 297/437 |
| 4,232,681 | 11/1980 | Tulaszewski | 128/653 |
| 4,373,709 | 2/1983 | Whitt | 128/882 |
| 4,407,277 | 10/1983 | Ellison | 128/82 |
| 4,426,071 | 1/1984 | Kleustad | 269/328 |
| 4,443,005 | 4/1984 | Sugarman et al. | 269/328 |
| 4,526,355 | 7/1985 | Moore | 269/328 |
| 4,545,573 | 10/1985 | Murphy | 269/328 |
| 4,549,540 | 10/1985 | Caspari | 128/882 |
| 4,564,164 | 1/1986 | Allen | 269/322 |
| 4,579,324 | 1/1986 | McConnell | 269/328 |
| 4,624,245 | 11/1986 | Mullin | 269/328 |
| 4,796,846 | 1/1989 | Meier | 269/328 |
| 4,913,413 | 4/1990 | Raab | 269/328 |

Primary Examiner—Robert A. Hafer
Assistant Examiner—Michael Brown
Attorney, Agent, or Firm—Fish & Richardson

[57] ABSTRACT

An apparatus for adjustable positioning of a patient's leg during a medical procedure has a base which may be attached to an operating table, a pitch/jaw assembly mounted upon the base, a leg extension having a first end mounted upon the pitch/yaw assembly for movement of a second end in horizontal and vertical planes relative to the base, a strap of the like for securement of the lower end portion of the patient's leg, and a brace for fixed positioning of the patient's thigh. In preferred embodiments, a foot brace is rotatably mounted at the second end of the leg extension. Also, the leg extension is pivotable about the base in vertical and/or horizontal planes from a first position toward an adjustment position, the pitch/yaw assembly adapted to return the leg extension toward its first position, and therebeing a lock or the like for securing the leg extension in adjusted position.

19 Claims, 15 Drawing Sheets

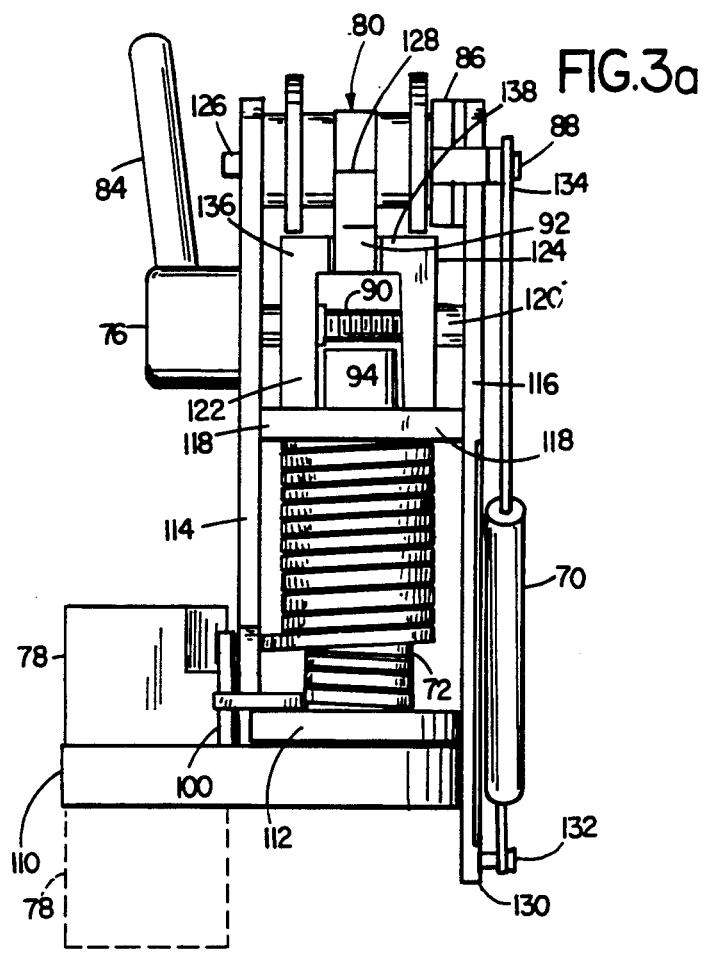
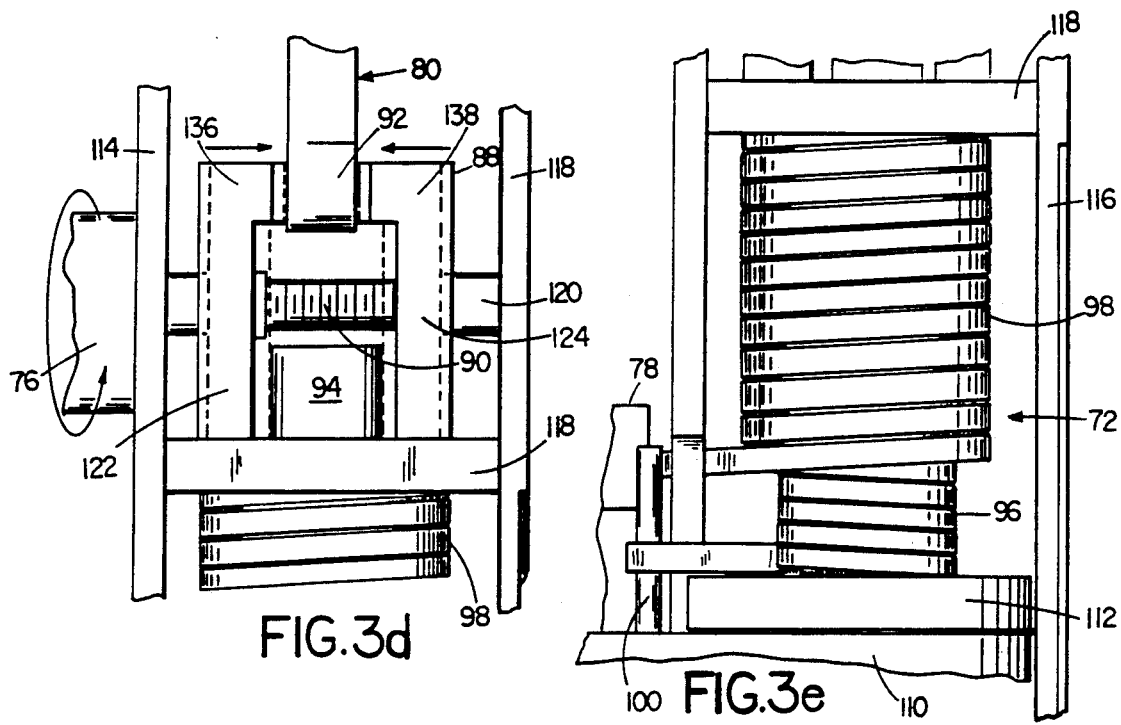

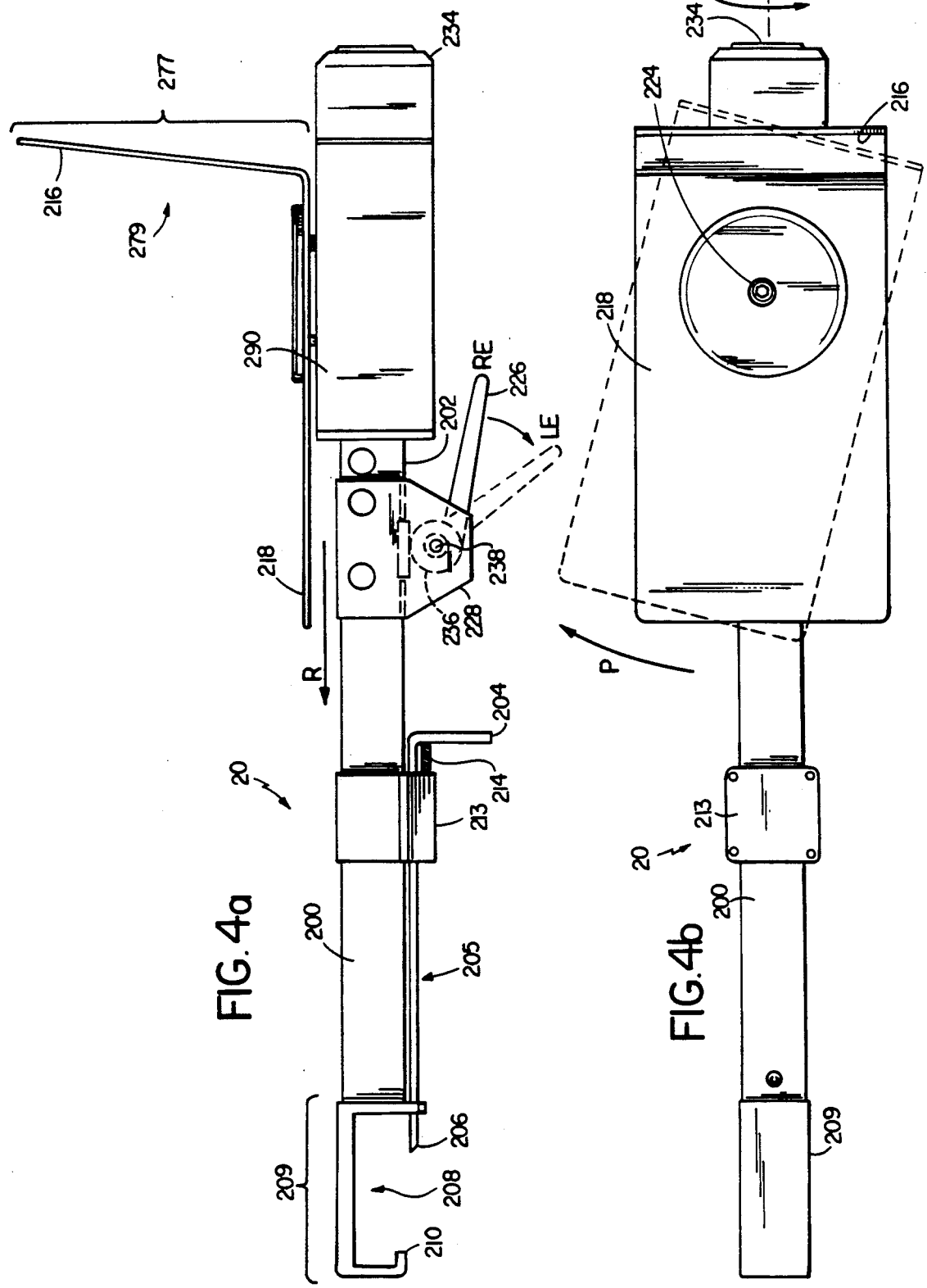

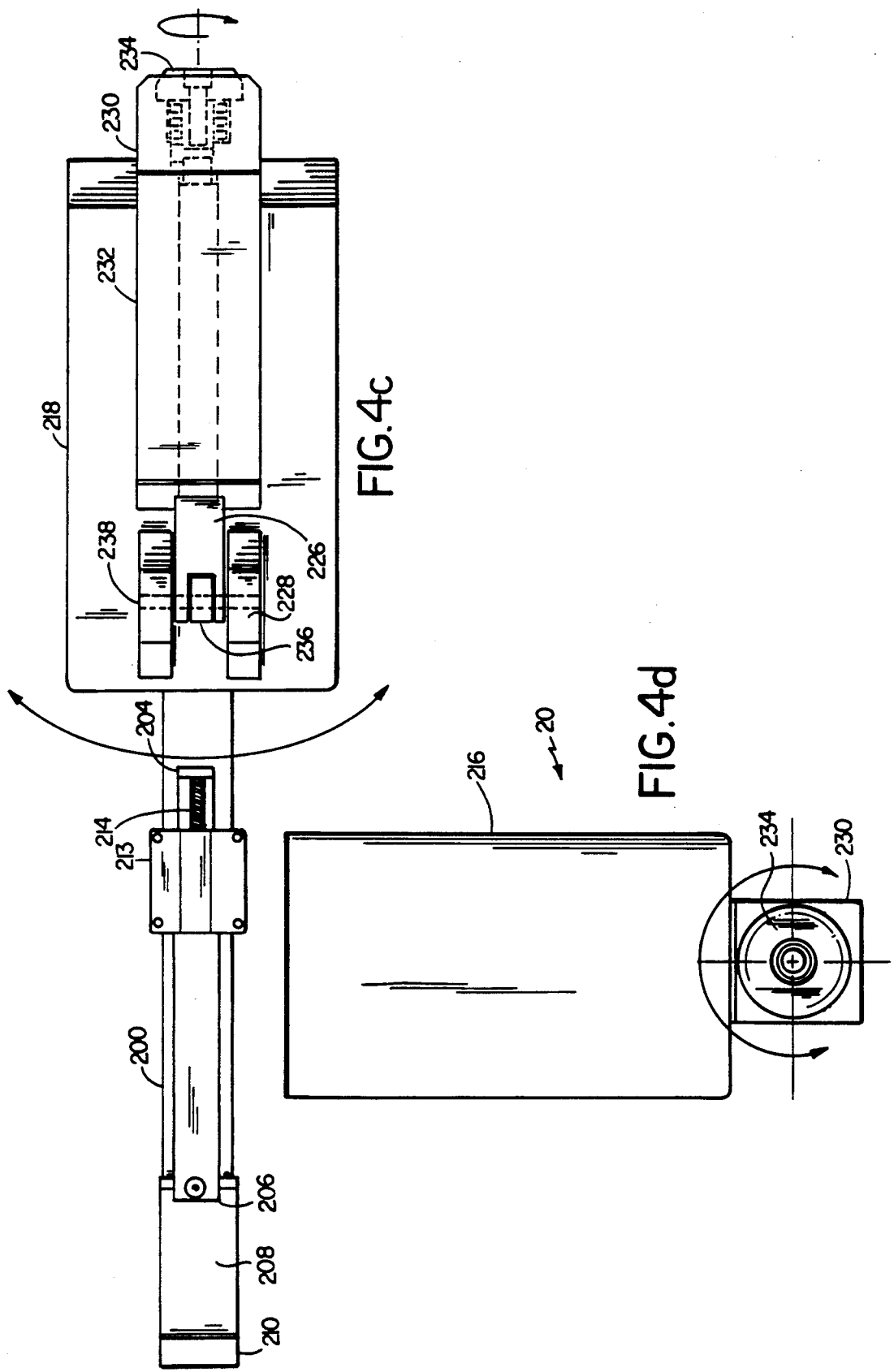

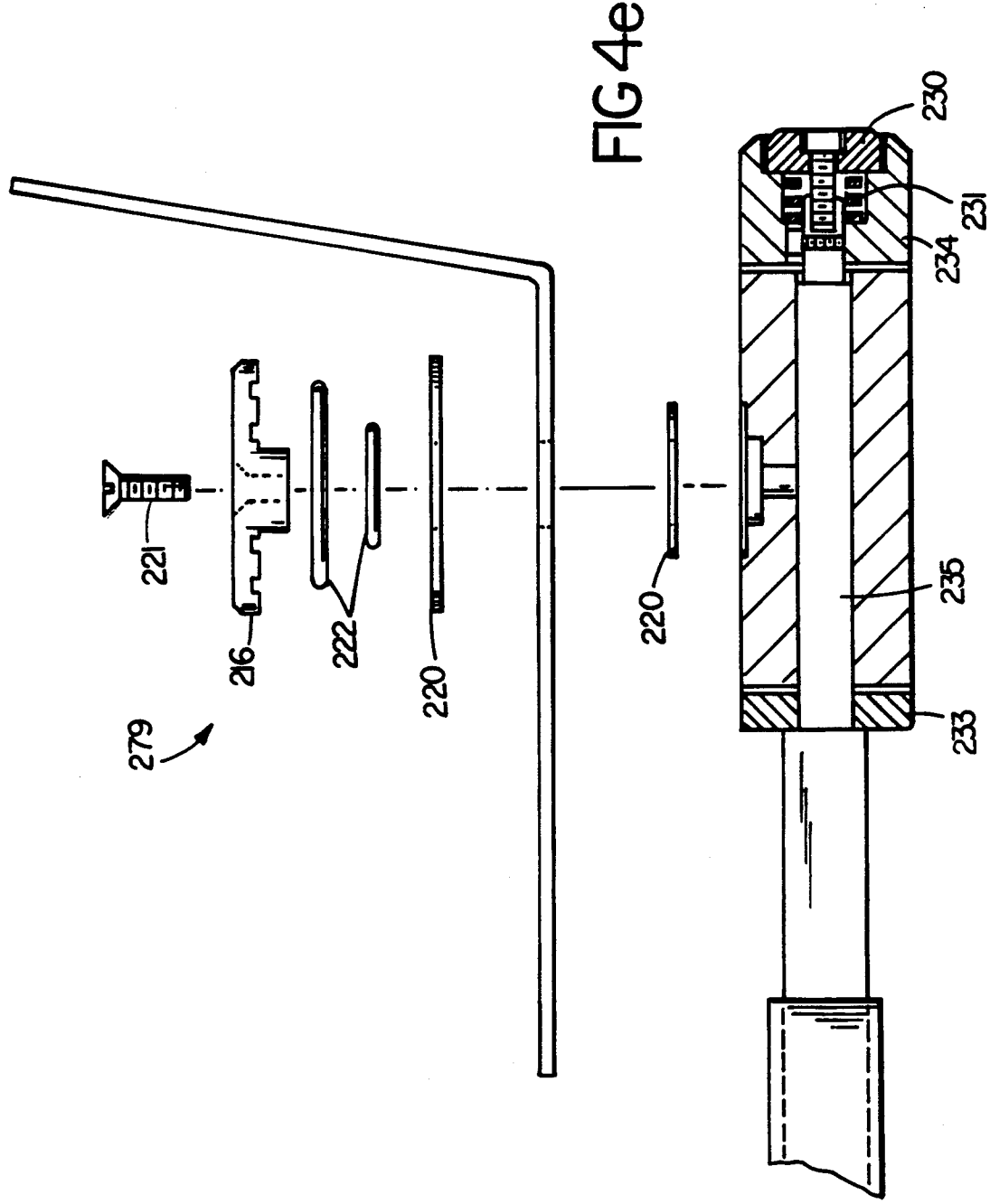

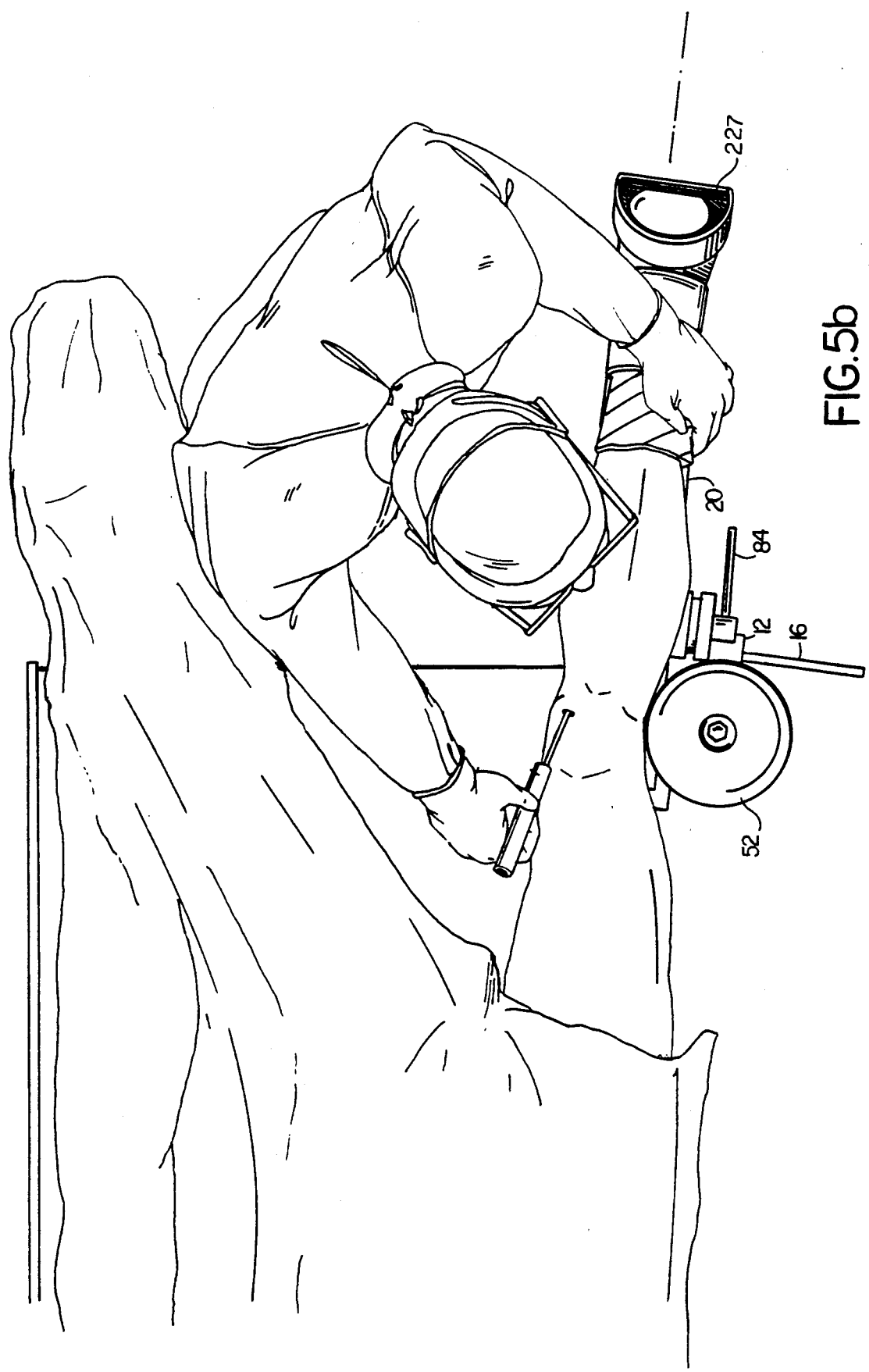

VARUS AND VALGUS LEG MANIPULATOR

BACKGROUND OF THE INVENTION

This invention relates to instruments for positioning body limbs during a medical procedure.

Although the human knee is a very strong joint, the joint can be damaged due to trauma or disease. The knee is a complex joint composed of three articulating surfaces; the two condyles of femur with the corresponding tuberosities of the tibia and the patella with the femur. The bones of the knee are held in place by six exterior ligaments and six interior ligaments and are cushioned from each other by membranous sacks, the bursae. In addition, the semilunar fibro-cartilage deepen the surface of the head of the tibia for articulation with the femur and thereby strengthen the joint. Frequently surgical intervention can correct damage sustained by elements of the knee. For example, bony portions of the knee may be replaced with synthetic components and soft tissue of the knee may be surgically repairable. Typically, an arthroscopic procedure may be used by the surgeon to visualize the joint prior to operating upon the knee joint.

In an arthroscopic procedure, the tip of a fiber-optic arthroscope is inserted into the joint, and by manipulating the leg, that is, moving the lower leg relative to the upper leg, the joint is maneuvered so the surgeon can see, e.g. on a video monitor, the structure of the joint prior to operating on it. Generally, the surgeon performing the arthroscopic procedure holds the leg to be examined by resting the calf of the patient's leg on the iliac crest of the surgeon's hip, or by placing the patient's foot on the femoral region of the surgeon's thigh. The surgeon, by moving his own body up and down and side to side, causes the patient's lower leg to move relative to the patient's thigh, and thereby manipulates the joint for examination or treatment. However, this method of manipulation results in fatigue for the surgeon, since the surgeon is forced to support the weight of the patient's leg while, at the same time, bending over the lower leg to position the arthroscope. Further, since there is no automatic returning of the knee from a valgus, away from the body's midline, or varus, toward the body's midline, manipulation to its normal position, the knee can undergo further damage if the surgeon moves the lower leg at too great an angle relative to the upper leg.

Previous supports for arthroscopic procedures such as described in U.S. Pat. No. 4,407,277 were capable of anchoring the leg in a given position once the leg was placed in the required position. However, these devices were simply braces which did not help the physician in placing the limb into the proper position nor did they return the limb to a normal orientation once the manipulation was complete.

The objectives of the present invention include providing a device that not only will maintain the limb in a predetermined position, but will reduce the stain on a physician in placing the limb in that position and will reduce the risk of overextending and thus further damaging the knee joint.

SUMMARY OF THE INVENTION

An apparatus for adjustable positioning of a patient's leg during a medical procedure has a base which may be attached to an operating table, a pitch/yaw assembly mounted upon the base, a leg extension having a first end mounted upon the pitch/yaw assembly for movement of a second end in horizontal and vertical planes relative to the base, a strap of the like for securement of the lower end portion of the patient's leg, and a brace for fixed positioning of the patient's thigh. In preferred embodiments, a foot brace is rotatably mounted at the second end of the leg extension. Also, the leg extension is pivotable about the base in vertical and/or horizontal planes from a first position toward an adjustment position, the pitch/yaw assembly adapted to return the leg extension toward its first position, and therebeing a lock or the like for securing the leg extension in adjusted position.

One aspect of the apparatus is that the pitch/yaw assembly has a base plate having a plane parallel to the plane of the operating table, and a cylinder extending perpendicularly from the base plate. A frame is rotatably mounted on the cylinder and capable of being locked in a predetermined orientation on the cylinder. An extension mount for removably mounting the leg extension section to the pitch/yaw assembly is rotatably mounted to the frame and is capable of locking the leg extension section in a given orientation relative to the extension mount.

Another aspect of the pitch/yaw assembly is a counter wound spring coaxial with the cylinder which returns the frame to a first horizontal orientation upon the cessation of a horizontal force. The extension mount includes an axle mounted within the frame and a semi-circular member attached to the axle. The semi-circular member has a notch, a lip and a pressure brake portion. The pitch/yaw assembly further includes a locking means capable of locking the frame in a predetermined orientation on the cylinder. The locking means have at least two locking arms movably attached to the frame and located on opposite sides of the cylinder. In one position the arms compress the cylinder and lock the frame in a predetermined orientation.

A further aspect of the locking arms is that each has an upper portion with the semi-circular member located between the upper portions, so as to lock the semi-circular member in a fixed orientation when the cylinder is compressed.

An additional aspect of the apparatus is that the leg extension portion includes an attachment mount, for removable attaching the distal end of the leg extension portion to the pitch/yaw assembly. An outer extension is attached to the attachment mount with an inner extension slidably mounted within and extending from the outer extension. An extension lock for holding the inner extension at a predetermined position within the outer extension is included. The extension lock includes a collar attached to said outer extension and a lever, pivotally mounted on the collar to cause a floating disk freely mounted within an opening in the outer extension, to press against the inner extension when the lever is in a first position and to not cause the floating disk to press against the inner extension otherwise.

Still another aspect includes a rail mounting bracket for mounting the apparatus for adjustable positioning of a patient's leg to a rail of an operating table. The rail mounting bracket includes a rail lock for fixedly attaching the mounting bracket to the rail of the operating table, a rail extension and a rail extension lock for attaching the rail extension to the rail lock. The rail extension lock includes a block defining a bore and having a groove on the surface of the block perpendicular to the bore. A locking lever is pivotally mounted in the block so as to partially obstruct the bore in one position and to leave the bore unobstructed in a second position.

Still yet another aspect of the invention is that the foot brace includes a foot block axle extending from the distal end of the leg extension and a foot block defining a bore and rotatably mounted on the foot block axle. A braking means for selectively reducing the ability of said foot block to rotate about the foot block axle is included. A varus/valgus pivot extends perpendicularly to the foot block axle and has a foot bracket rotatably mounted on it.

DESCRIPTION OF A PRESENTLY PREFERRED EMBODIMENT

We first briefly describe the drawings.

DRAWINGS

FIG. 2 is a perspective view of the rail extension and operating rail clamp portions of the apparatus of FIG. 1, while

FIG. 3 is a perspective view of the pitch/yaw assembly portion of the apparatus of FIG. 1, while FIGS. 3a, 3b and 3c are front and left and right side views, respectively, of the pitch/yaw assembly of FIG. 3;

FIG. 3d is an enlarged view of the locking mechanism of the pitch/yaw assembly of FIG. 3;

FIG. 3e is an enlarged view of the spring portion of the pitch/yaw assembly of FIG. 3;

FIG. 4 is a perspective view of the cantilever extension portion of the apparatus of FIG. 1, while FIGS. 4a, 4b, 4c and 4d are side, top, bottom and end views, respectively, of the cantilever extension shown in FIG. 4, and FIG. 4e is an exploded view of the foot brace of FIG. 4;

FIG. 5b is a top diagrammatic view of the instrument in use with a patient, with the manipulator holding the patient's leg in neutral position.

Figure 1:
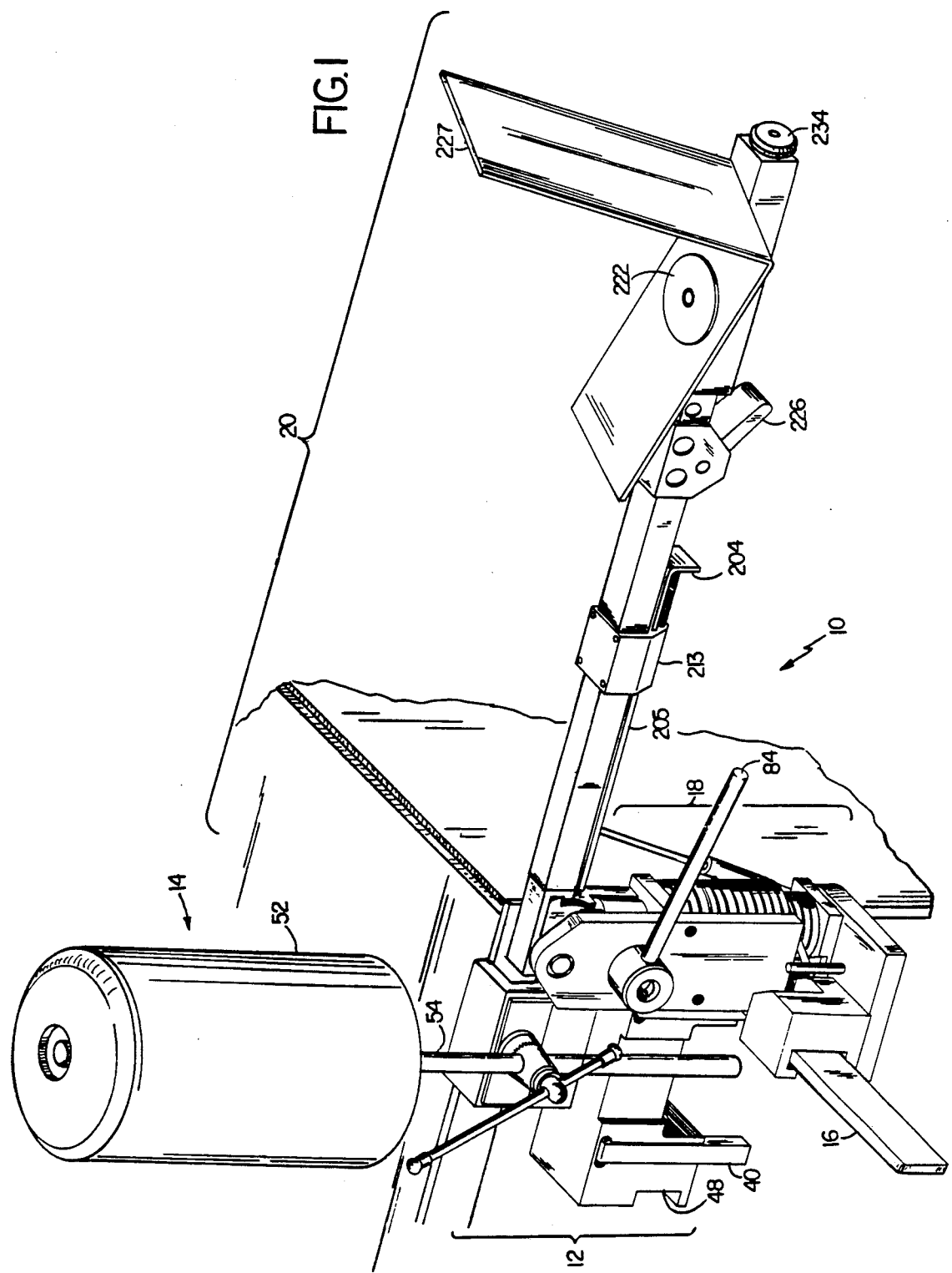
FIG. 1 is a perspective view of a leg manipulation apparatus of the invention.

Referring to FIG. 1, a leg manipulation assembly 10 of the invention includes rail clamp portion 12, a thigh rest portion 14, a rail extension portion 16, a pitch/yaw assembly 18 and a cantilevered extension portion 20.

Figure 2:
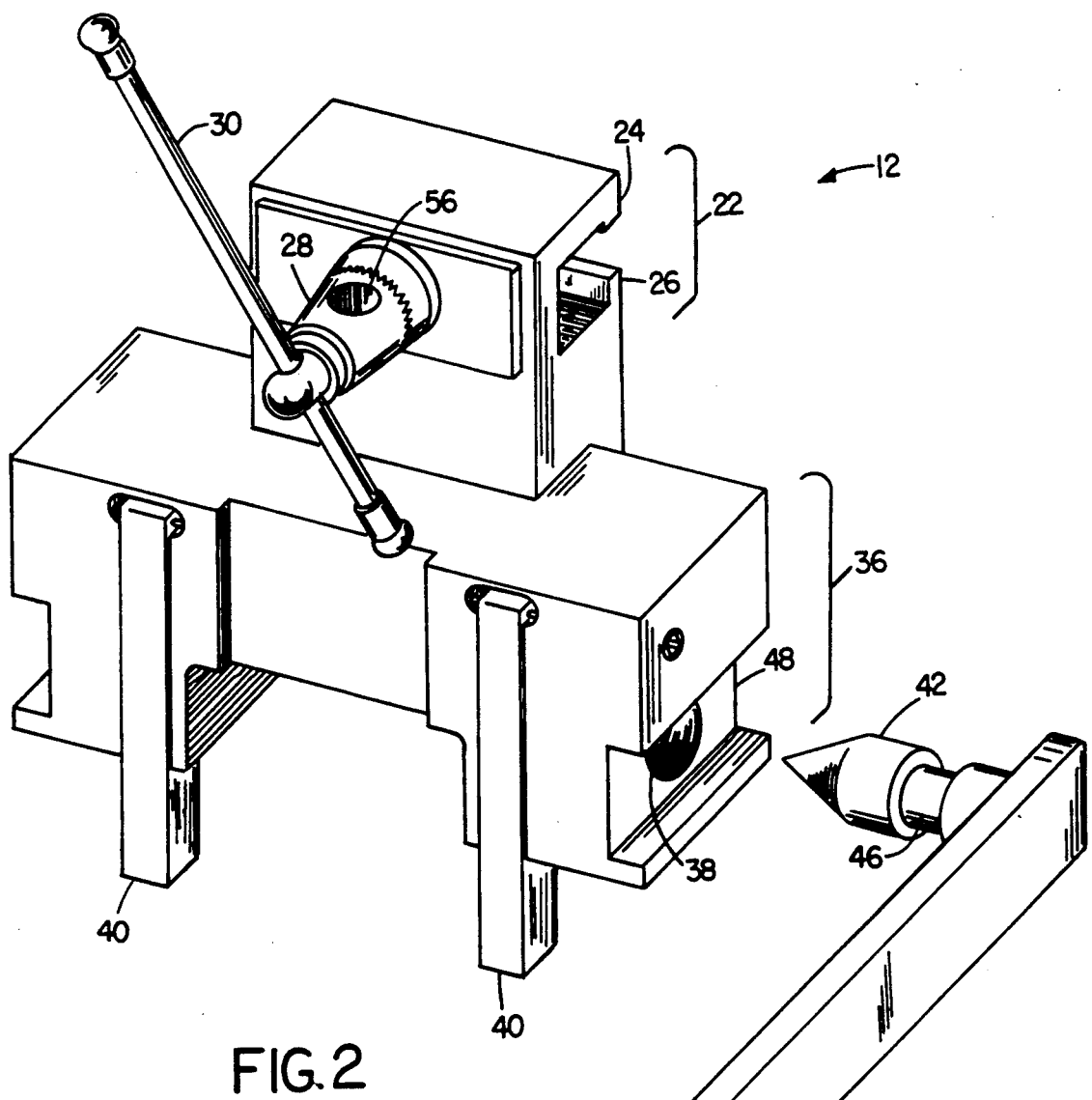
Figure 2A:
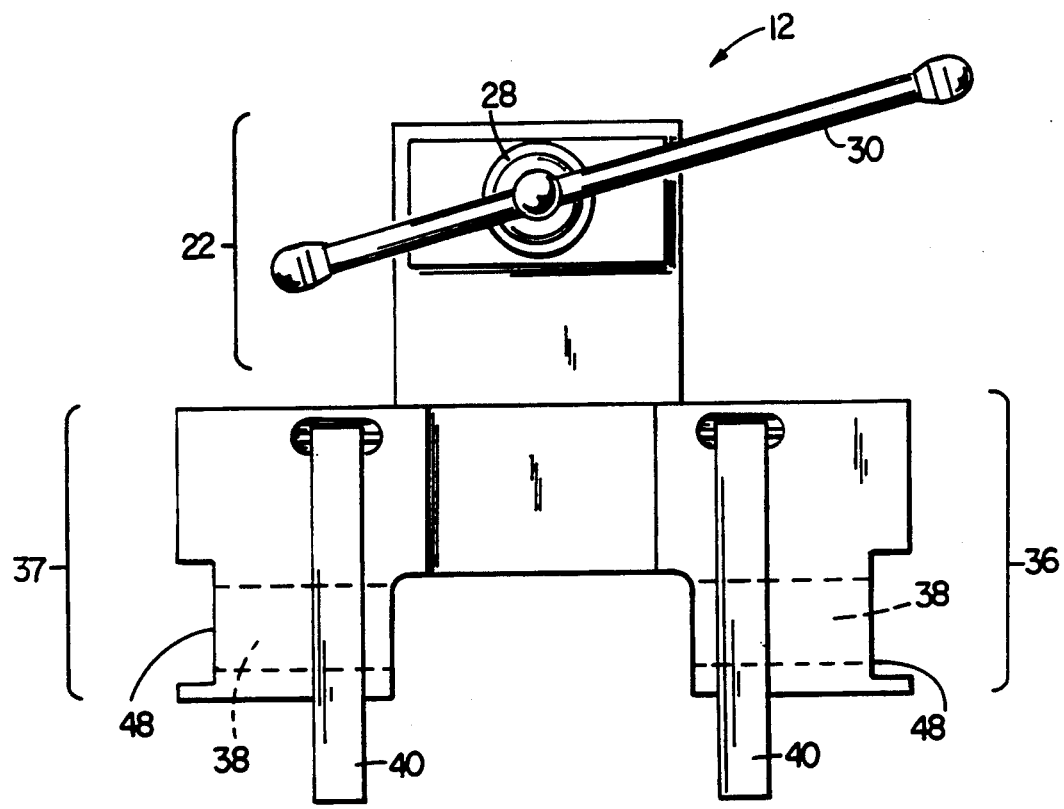
FIGS. 2a and 2b are respective front and side views of the operating rail clamp portion of FIG. 2, and FIGS. 2c and 2d are respective front and side views of the rail extension portion of FIG. 2.
Figure 2B:
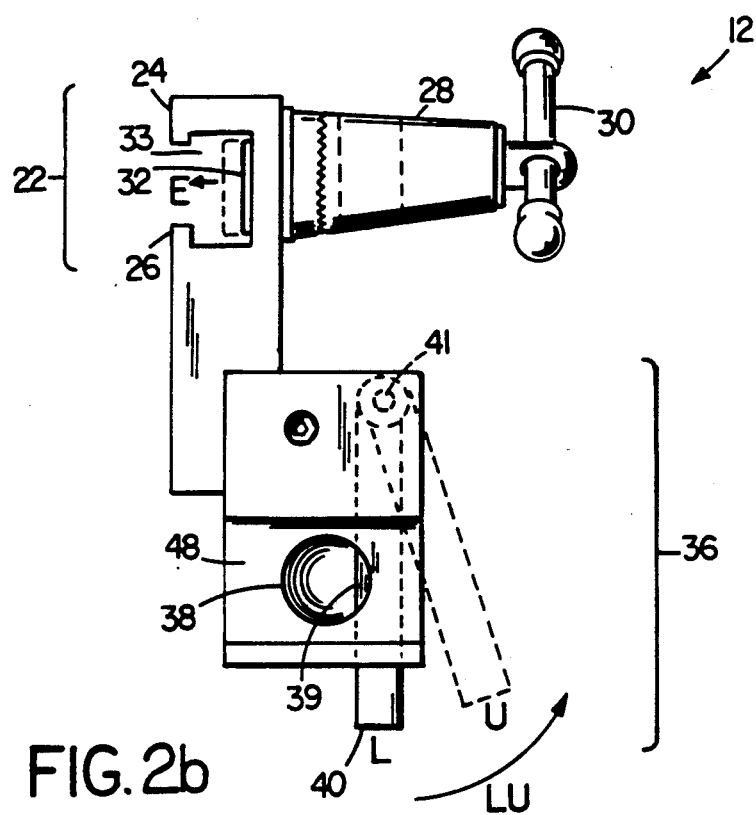

Referring to FIGS. 2 et seq., the rail clamp portion 12 includes a rail clamp body 22 adapted to engage upon an operating table rail. The operating table rail (not shown) passes through a groove 33 defined by the body 22 between an upper lip 24 and a lower lip 26 of the rail clamp body 22. A clamp socket 28, affixed to the rail clamp body 22, has a plunger portion 32 (FIG. 2b) which extends from the groove 33 through the body 22 to a locking handle 30. When the clamp socket 28 is tightened by rotating the locking handle 30, the plunger 32 extends (arrow E) into the groove 33 and holds the operating table rail firmly against the inner shoulder surfaces of the upper lip 24 and the lower lip 26 of the rail clamp body 22.

The rail clamp portion 12 also includes two rail extension segments 36 and 37 for engaging a rail extension portion 16. Each of the rail extension segments 36 and 37 defines a bore 38 and a rail extension lock 40, adapted for rotation (arrow LU) about a locking lever pivot 41. When the rail extension lock 40 is in the unlock position U, the bore 38 is unobstructed. When the rail extension lock 40 is in the lock position L, the bore 38 is partially obstructed 39 by the rail extension lock 40.

Figures 2C, 2D:
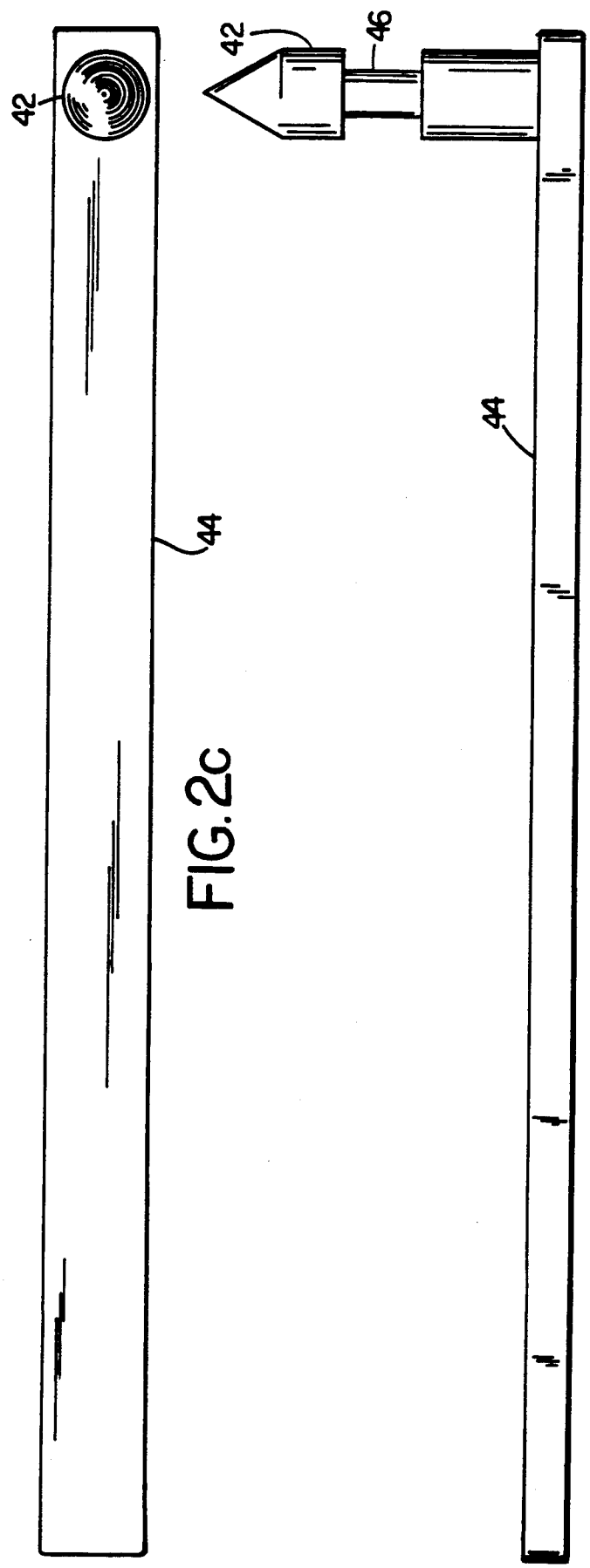

Referring also to FIGS. 2c and 2d, the rail extension portion 16 includes a rail extension piston 42 extending perpendicularly from one end of a rail body 44. The rail extension piston 42 has a cylindrical body with a conical end 45, the central portion 46 of the cylindrical body being of reduced diameter. When positioned on the rail clamp portion 12, the rail extension piston 42 is located within the bore 38, such that when the rail extension lock 40 is in the locked position, the rail extension lock 40 seats within the reduced diameter central portion 46 of the rail extension piston 42. The engagement of the radial surfaces boundary of the reduced diameter central portion 46 with the rail extension lock 40 prevents the removal of the rail extension piston 42 from the bore 38. The reduced diameter central portion 46 of the rail extension piston 42 can only engage the rail extension lock 40 when the rail body 44 seats within a rail extension slot 48 in the rail extension segment 36 such that the rail extension portion 16 extends at right angles to the operating table rail.

The rail extension segment 36 of the rail clamp portion 12 is symmetrical about a plane through the clamp socket 28 and parallel with the rail extension 36. In this way, the rail clamp portion 12 can be used on a rail on either side of the operating table.

The thigh rest portion 14 includes a padded cylindrical thigh rest 52 affixed to the end of a thigh rod 54. When in position, the thigh rod 54 is inserted in the clamp socket bore 56 of the clamp socket 28 of the rail clamp portion 12. The tightened clamp socket 28 locks both the rail clamp 12 to the operating table rail and the thigh rod 54 to the rail clamp portion 12. In this way the height of the padded cylindrical thigh rest 52 can be adjusted.

Figure 3:
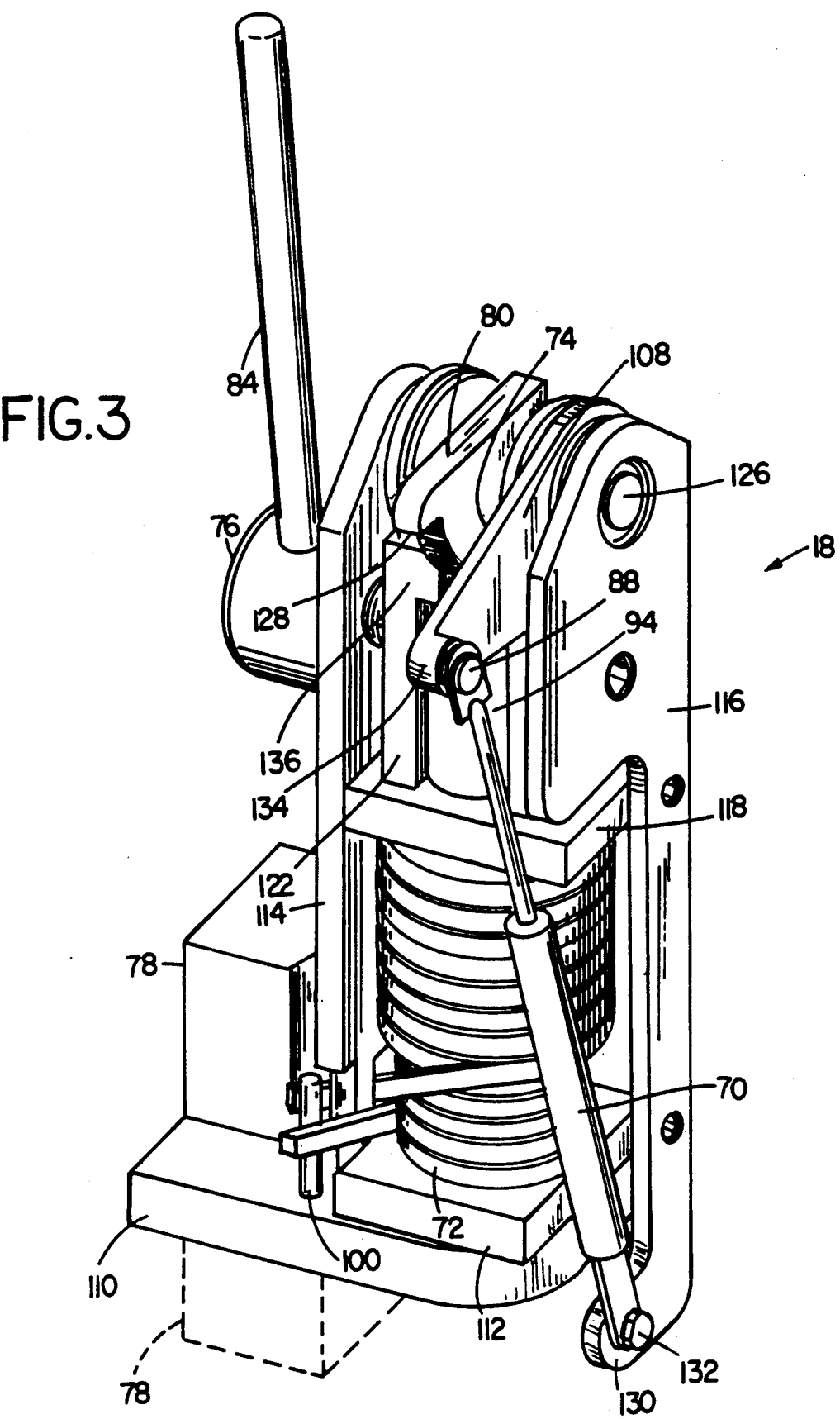
Figure 3C:
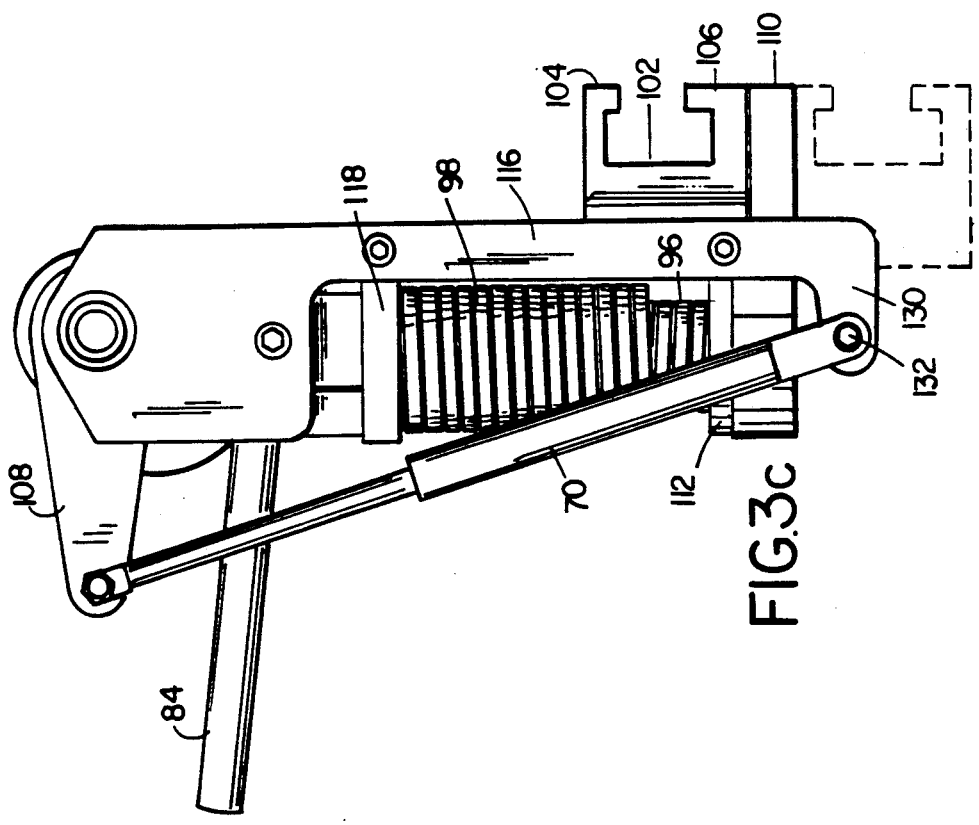
Figure 3B:
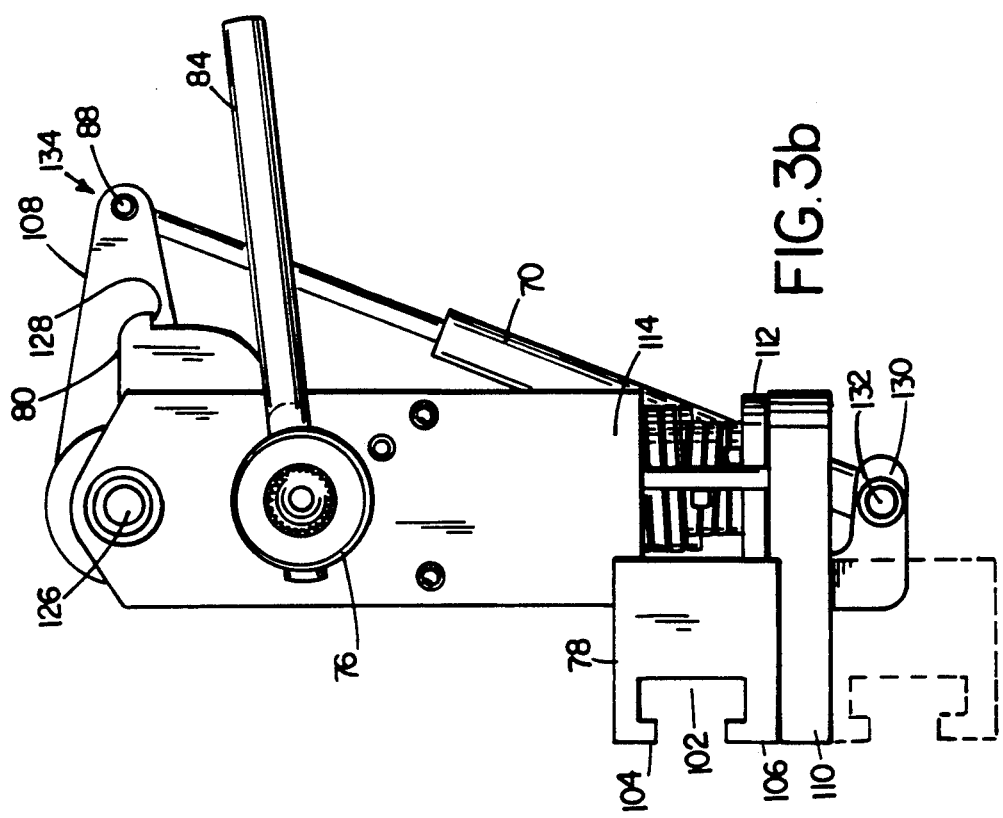

Referring to FIG. 3, and to FIGS. 3a–3e, the pitch/yaw assembly 18 comprises a spring assembly 72, a piston assembly 70 and a mounting block 78 attached to a base plate 110. The mounting block 78 can be attached to either the upper surface of the plate 110 or the lower surface of the plate 110 (as shown in phantom in FIGS. 3a, 3b and 3c) as determined by the type of operating table, i.e. the vertical location of the operating table rail, to which it is to be affixed. The mounting block 78 defines a groove 102, having an upper lip 104 and a lower lip 106, which permit the pitch/yaw assembly 18 to be slidably mounted to the rail body 44 of the rail extension portion 16. Attached to and extending perpendicularly from the base 110 is a cylinder 94. A base 112 is rotatably mounted upon cylinder 94 and rests upon base plate 110. One end of a left arm support 114 and one end of a right arm support 116 are attached to base 112 to extend perpendicularly from the base 112, and are attached to a spring retaining plate 118 located between the arms 114 and 116 and positioned approximately half way up their length. The spring retaining plate 118 is also rotatably mounted on cylinder 94. Thus the base 112, the left and right support arms 114 and 116 respectively, and the spring retaining plate 118 form a frame capable of rotating about the cylinder 94.

Surrounding cylinder 94 and resting upon base 112 is the counter-wound spring 72 having an inner portion 96 and an outer portion 98. One end of the spring portions 96 and 98 are prevented from rotating by a rod 100 affixed to the base plate 110. The other ends of the inner portion 96 and the outer portion 98 of the counter-wound spring 72 are attached to the spring retaining plate 118. The counter-wound spring is attached to the spring retaining plate 118 and the rod 100 in a manner such that a clock-wise rotation (as viewed from above) of the base 112, causes the inner spring portion 96 to tighten and a counter-clockwise rotation (as viewed from above) of the base 112 causes the outer spring portion 98 to tighten. In this way, under either clockwise or counter-clockwise rotation, one spring portion is tightened and the counter-wound spring 72 is biased to its neutral position. Thus by virtue of its attachment to the spring retaining plate 118, the counter-wound spring 72 also causes the frame comprising the base 112, the left support arm 114, the right support arm 116 and the spring retaining plate 118, to return to its initial orientation. The initial orientation is chosen such that the opening in defined by the frame points perpendicular to the rail extension portion 16.

A pitch/yaw lock 84 is attached to a hub 76 which in turn is attached to an axle 120 passing between the right support arm 116 and left support arm 114. The central portion 90 of the axle 120 threaded. Threaded upon the threaded portion 90 of axle 120 is a left locking arm 122 and a right locking arm 124. The locking arms 122, 124 are counter threaded such that when the hub 76 is rotated (arrow R), the arms 122, 124 move in opposite directions (arrows C). When in the unlocked position UR, the left locking arm 122 and the right locking arm 124 are positioned a small distance away from the upper portion of cylinder 94. When the arms 122, 124 are in the locked position LR (shown in dotted lines), the arms 122, 124 compress the cylinder 94 and prevent frame from rotating about the axis of the cylinder 94.

An extension pivot pin 126 passes through the upper ends of the support arms 114, 116 opposite the base 112. Fixed to the extension pivot pin 126 is a piston arm 108 and an extension mount 80. The extension mount 80 includes an extension mounting lip 128, an extension notch 129 and a pressure brake portion 92. A gas piston 70 is connected between the upper piston mount 134 of the piston arm 108 and the lower piston mount 130 of the right support arm 116 by rotatable pivot pins 88 and 132 respectively. The gas piston 70 dampens the rotation of the piston arm 108 and also dampens the rotation of the extension pivot pin 126.

When the locking arms 122, 124 are in the locked position LR (FIG. 3d), the upper portions 136, 138 of the locking arms 122, 124 grip the pressure brake portion 92 of the extension mount 80, preventing rotation of the pivot pin 126. To insure that the locking arms 122, 124 can grip both the cylinder 94 to prevent rotation about the cylinder 94 and the pressure brake portion 92 of the extension mount 80, to prevent rotation about the pivot pin 126, the upper portions 136, 138 of the locking arms are constructed such that when the locking arms 122, 124 first engage the cylinder 94, the upper portions do not quite engage the pressure brake portion 92 of the extension mount 80. Additional tightening of the locking arms causes the locking arms to slightly rotate about the upper end of the cylinder 94 causing the upper portions of the locking arms 122, 124 to grasp the pressure brake portion 92 of the extension mount 80 tightly. Thus, using a single handle 84, both the angular orientation of the frame relative to the rail extension portion 16 and the azimuthal orientation of the extension mount 80 relative to the plane of the base plate 110 can be locked. Additionally, by adjusting the pressure of the locking arms 122, 124, against the cylinder 94 and the pressure brake portion 92 of the extension mount 80, the azimuth of the extension mount 80 and the orientation of the frame can be changed with greater of lesser difficulty.

Figure 4:
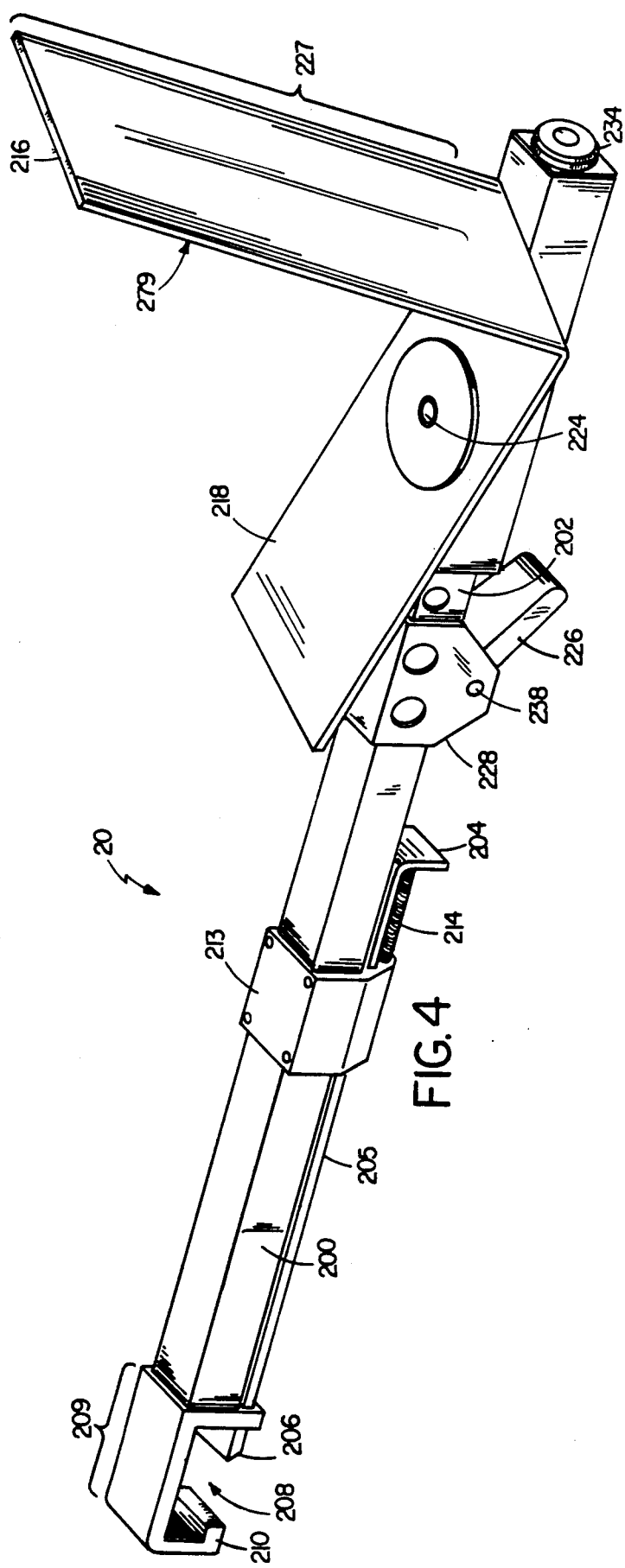

Referring to FIGS. 4 and to FIGS. 4a-4d, the cantilevered extension portion 20 includes a pitch/yaw mounting bracket 209, in engagement with the pitch/yaw assembly 18. The mounting bracket 209 includes a fixed lip 210, a bridge section 208, and a movable lip 206. The mounting bracket 209 is attached to an outer extension 200. The movable lip 206 is one end of an L-shaped release 205 which is slidably attached to the outer extension 200 through a release collar 213. The cantilever release 204 of the L-shaped release 205 projects away from the outer extension 200 and is biased toward the release collar 213 by a spring 214. The spring 214 therefore causes the L-shaped release 205 to be biased toward the mounting bracket 209 causing the movable lip 206 to extend toward the fixed lip 210. Therefore, when mounted on the pitch/yaw assembly 18, the fixed lip 210 engages the extension notch 129 of the extension mount 80, and the movable lip 206 engages the extension mount lip 128 of the extension mount 80. When the movable lip 206 is retracted away from the fixed lip 210, the cantilevered extension portion 20 can be rotated about the fixed lip 210 and removed from the pitch/yaw assembly 18.

An inner extension 202 is slidably mounted within the outer extension 200, through an extension release collar 228. An extension lock 226 is rotatably mounted in the extension release collar 228 by an extension lock pivot 238. When the extension lock is in the position designated LE, the upper portion of the extension lock 226, comprising a cam 236 mounted eccentrically to extension lock pivot 238, is pressed against a floating disk 237 retained within outer extension 200 and adjacent the inner extension 202. This forces the floating disk 237 against the inner extension 202 and preventing it from moving within the outer extension 200.

Referring to FIG. 4e, the foot brace 277 is attached an ankle block 232 mounted to the end of the inner extension 202 which extends out from the outer extension 200. The foot brace 277 includes an L-shaped foot rest plate 279 having a heel rest portion 218 and a plantar surface portion 216. The heel rest portion 218 is attached to the ankle block 232 by a valgus/varus pivot 224 comprising a pair of o-rings 222 located between a pressure plate 220 and a friction washer 220 and held in place by a retaining screw 221. This arrangement permits the L-shaped plate foot rest plate 279 to rotate (as indicated by the arrow P) about an axis perpendicular to the plane of the heel rest portion 218, and yet be held with enough friction so as to maintain the foot rest in a given orientation.

The ankle block 232 is rotatably mounted on an block axle 235. The block axle 235 is fixedly attached to the inner extension 202. A proximal brake shoe 233 is also attached to the inner extension 202 coaxially with the block axle 235. The ankle block 232 abuts the proximal brake shoe 233. A distal brake shoe 234 is mounted distally to the ankle block 232 on the block axle 235. The ankle block 232 is therefore positioned between the two brake shoes 233 and 234, and prevented from rotating about the block axle 235 when the brake shoes 233 and 234 squeeze the ankle block 232. A clamp washer 230 mounted to the block axle retains a compression spring 231 against the distal brake shoe 234, forcing the distal brake shoe 234 against the ankle block 235, and forcing the ankle block 232 against the proximal brake shoe 233. By adjusting the compression of the compression spring 231, the amount of pressure with which the ankle block 235 is held is adjusted, thereby increasing or decreasing the ability of the ankle block 232 to rotate about block axle 235.

To use the leg manipulation assembly 10, the rail clamp portion 12 is positioned on the rail of the operating table on the side of the table corresponding to the leg to be examined. Once the rail clamp portion 12 is positioned on the operating table rail, the rod 54 of the thigh rest 14 is placed into the clamp socket bore 56 of the clamp socket 28 and the height of the padded cylindrical thigh rest 52 is adjusted by moving the rod 54 of the thigh rest 14 within the clamp socket 28. Once the proper height of the thigh rest 14 is realized, the thigh rest 14 is locked at that height and the rail clamp 12 is locked on the operating table rail by tightening the clamp socket 28 by turning the clamp socket handle 30. The position of the rail clamp 12 on the rail of the operating table is such that the thigh rest 14 is at corner of the operating table. In this way, the knee to be examined is flexed over the front of the table approximately adjacent to the thigh rest 14.

The rail extension portion 16 is then positioned by sliding the rail extension piston 42 into the bore 38 and aligning the rail body 44 with the rail extension slot 48 in the rail extension portion 36. Once the rail extension body 44 is seated within the rail extension slot 48, the rail extension lock 40 engages the reduced diameter 46 of the rail extension piston 42 to prevent the removal of the rail extension 16 from the rail clamp portion 12.

The mounting block groove 103 of the mounting block 78 of the pitch/yaw assembly 18 is slid along the rail extension body 44 until the pitch/yaw assembly 18 is adjacent to the rail clamp portion 12. Sterile drapes are then placed over the pitch/yaw 18 assembly, rail clamp portion 12 and rail extension portion 16.

The cantilever release 205 of the cantilever extension 20 is moved so as to retract the movable lip 206. The fixed lip 210 of the cantilever extension 20 is positioned in the extension notch 129 of the extension mount 80 of the pitch/yaw assembly 18 and the cantilevered extension 20 is rotated downward so as to bring the bridge section 208 against the top portion of the extension mount 80. The cantilever release 205 is then released and the spring 214 biases the movable lip 206 back toward the fixed lip 210 thereby engaging the extension mounting lip 128 and attaching the cantilever extension 20 to the pitch/yaw assembly 18.

The patient is placed on the operating table and the thigh of the leg to be examined is secured to the thigh rest 14. The extension lock 226 of the cantilever extension is moved upward (position RE in FIG. 4a) permitting the inner extension 202 to slide within the outer extension 200. The position of the inner extension 202 is then adjusted axially to conform the length of the cantilever extension 20 to the length of the patient's leg. Once the proper length is obtained, the extension lock 226 is moved downward (position LE in FIG. 4a) locking the inner extension 202 against the outer extension 200. The foot of the leg to be examined is placed against the foot brace 277 and held in place with a patient boot (FIG. 5a).

The doctor, directing the leg manipulator with the his right hand can use his left hand to move the pitch/yaw lock 84, to lock and unlock the right and left locking arms 124, 122 and thereby prevent or permit rotation in the plane of the operating table or rotation perpendicular to the plane of the table. Further, the physician can cause rotations about the valgus/varus pivot and the block axle simply by applying enough pressure to overcome the frictional resistance.

Figure 5A:
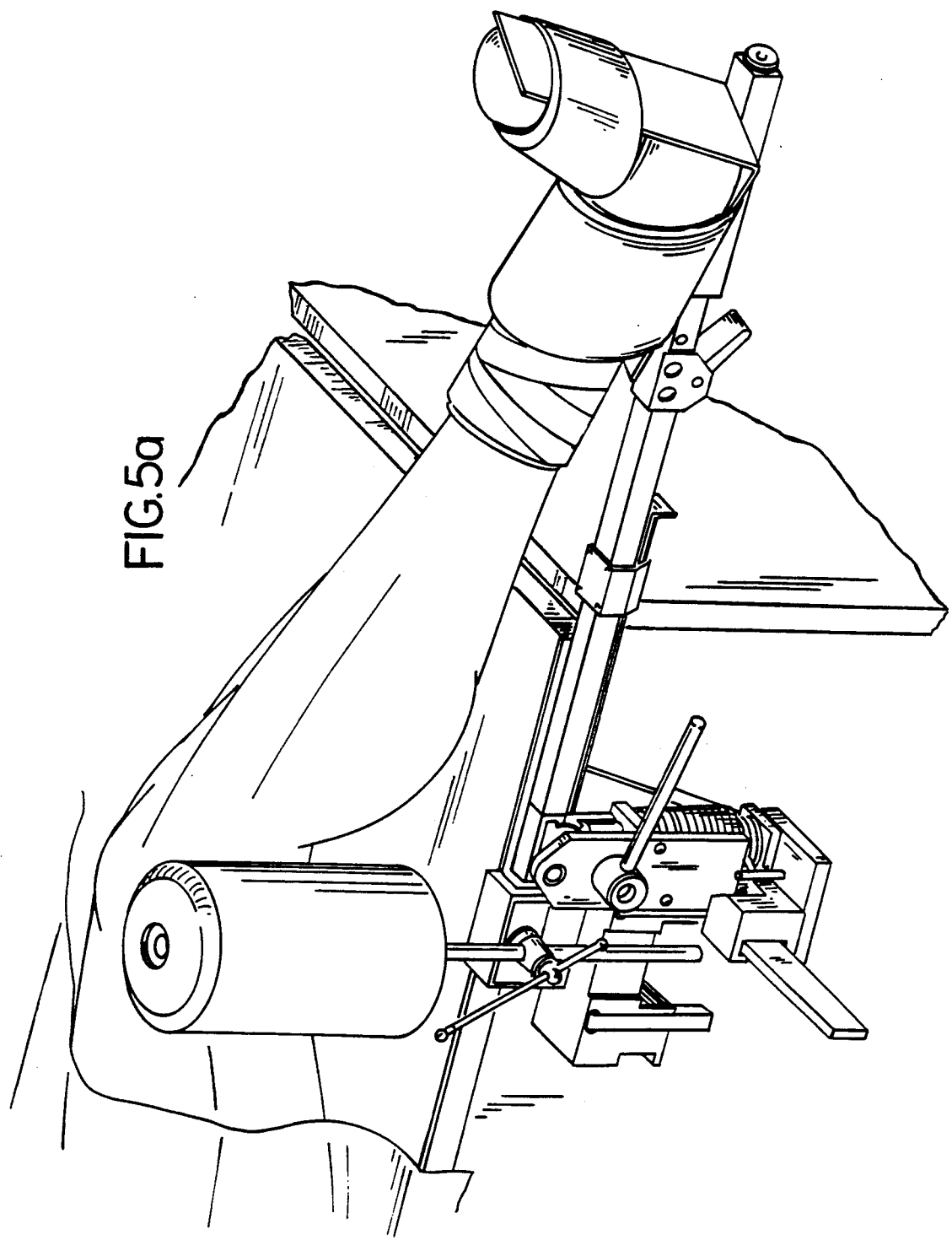
FIG. 5a is a perspective view of the instrument in use with a patient, with the manipulator is in neutral position.
Figure 5C:
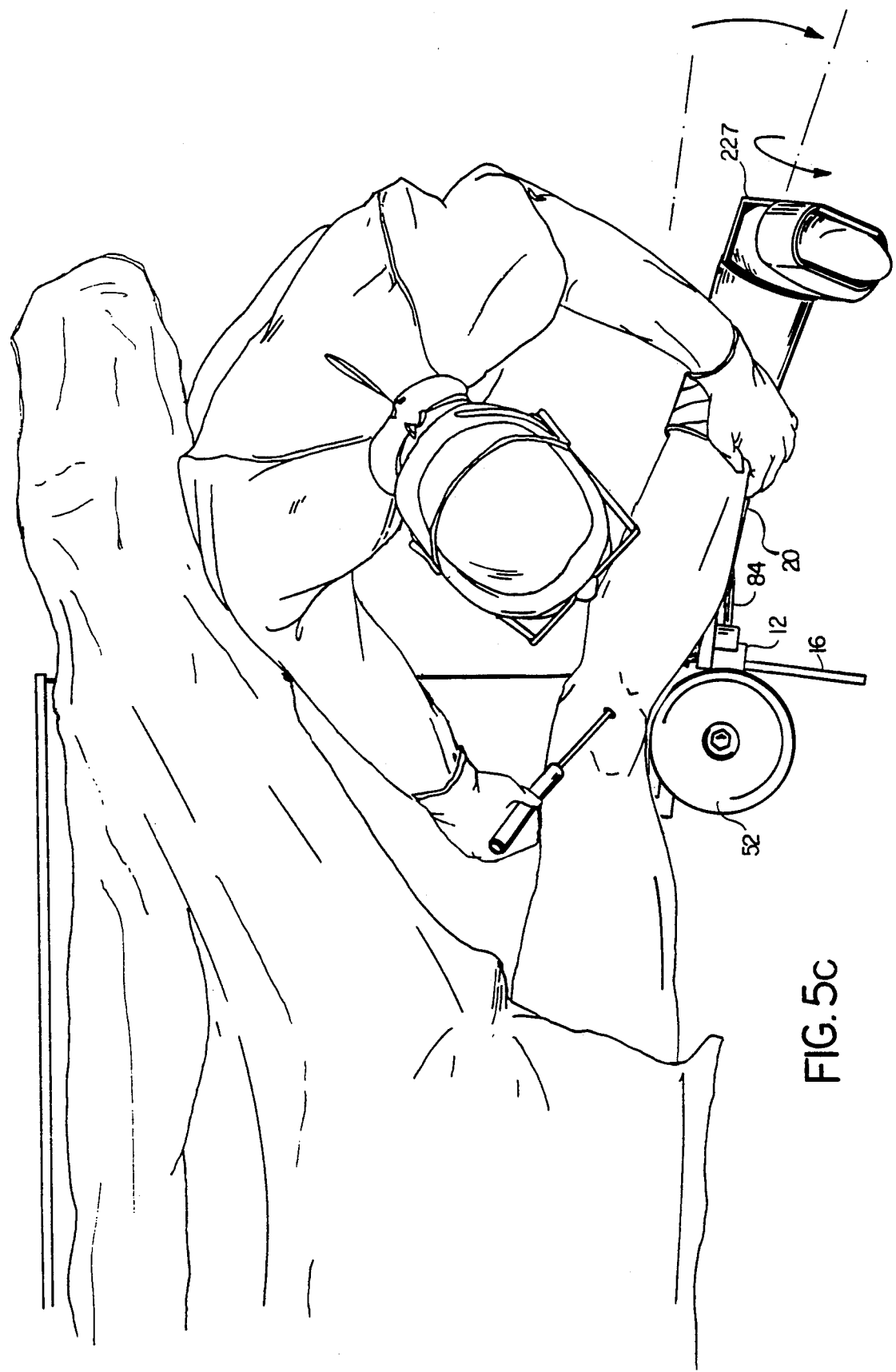
FIG. 5c is a top diagrammatic view of the instrument in use with a patient, with the manipulator holding the patient's leg in a varus position.
Figure 5D:
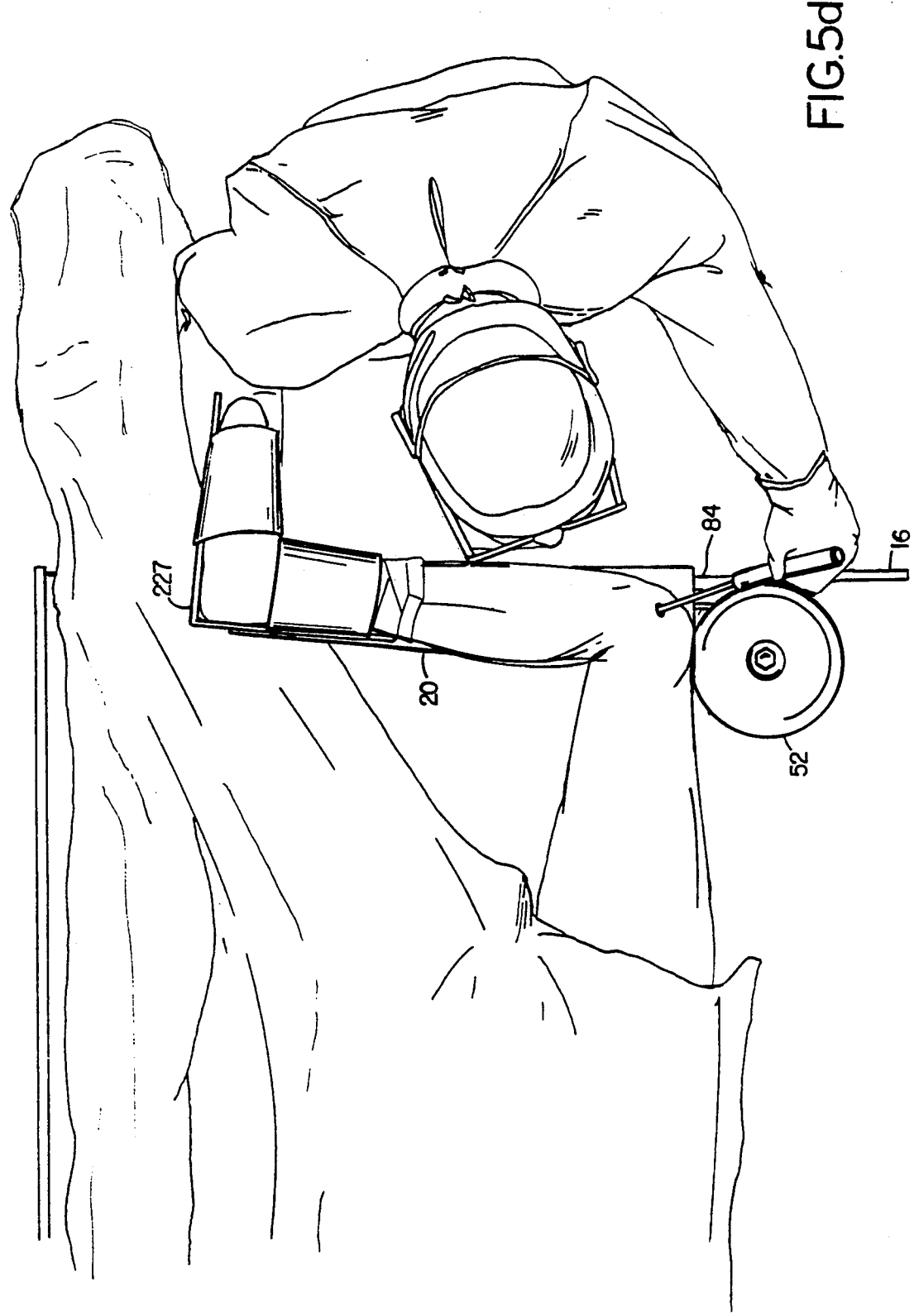
FIG. 5d is a top diagrammatic view of the instrument in use with a patient, with the manipulator holding the patient's leg in a figure four position.

Referring to FIGS. 5b and 5c, by loosening the pitch/yaw lock 84, the physician can cause movement in the plane of the operating table, and the leg manipulator will return the patient's leg to its normal position when the pressure by the physician is released. Once the proper angle and elevation of the leg is completed, the doctor can lock that position by adjusting the pitch/yaw lock 84. FIG. 5b shows a top diagrammatic of a patient on an operating table with the patient's left leg positioned against the thigh rest cylinder 52 and the patient's left foot on the foot brace 277. In order to clearly show the components of the manipulator, the device is shown undraped. In this view, the manipulator is in its neutral position. In FIG. 5c, the patient's leg has been moved into a varus position. Unless fixed in this position, by the tightening of the pitch/yaw lock 84, the pitch/yaw assembly automatically will bring the leg back to its neutral position as shown in FIG. 5a. In FIG. 5d the patient's leg has been moved into a figure four position. Again the pitch/yaw assembly automatically will bring the leg back to its neutral position as shown in FIG. 5a unless the pitch/yaw lock 84 is tightened.

One skilled in the art will realize that other embodiments are with the scope and spirit of the embodiment and as such the invention is limited only by the claims.

What is claimed is:

1. An apparatus for adjustable positioning of a patient's leg during a medical procedure, comprising
    a base;
    means for attachment of said base to an operating table;
    a pitch/yaw assembly mounted upon said base;
    a leg extension having a first end and a second end, said first end mounted upon said pitch/yaw assembly for pivoting movement of said second end in horizontal and vertical planes relative to said base;
    means associated with said second end for securement of the lower end portion of the patient's leg; and
    means for fixed positioning of the patient's thigh.

2. The apparatus of claim 1 wherein said means for securement is a foot brace mounted for rotation upon the second end of the leg extension.

3. The apparatus of claim 2 wherein said foot brace comprises:
    a foot block axle extending from said distal end of said leg extension;
    a foot block defining a bore, said foot block rotatably mounted on said foot block axle;
    a braking means for selectively reducing the ability of said foot block to rotate about said foot block axle;
    a varus/valgus pivot extending from said foot block perpendicularly to said foot block axle; and
    a foot bracket rotatably mounted on said varus/valgus pivot.

4. The apparatus of claim 3 wherein said braking means comprises:
   a first brake shoe fixedly attached to said foot block axle proximal to said foot block;
   a second brake shoe movably attached to said foot block axle distal to said foot block; and
   a compression spring assembly fixedly attached to said foot block axle, said compression spring assembly for forcing said second brake shoe against said foot block and said foot block against said first brake shoe.

5. The apparatus of claim 1 wherein said leg extension, having a first vertical position relative to said base, moveable from said first vertical position to an adjusted vertical position by application of force, further comprises:
   said pitch/yaw assembly adapted to return said leg extension toward said first vertical position; and
   means for securement of the leg extension in said adjusted vertical position.

6. The apparatus of claim 1 or 5 wherein said leg extension, having a first horizontal position relative to said base, moveable from said first horizontal position to an adjusted horizontal position by application of force, further comprises:
   said pitch/yaw assembly adapted to return said leg extension toward said first horizontal position; and
   means for securement of the leg extension in said adjusted horizontal position.

7. The apparatus of claim 1 wherein the pitch/yaw assembly comprises:
   a base plate having a plane parallel to the plane of the operating table, and having a cylinder extending perpendicularly from the base plate;
   a frame rotatably mounted on said cylinder, said frame being capable of being locked in a predetermined orientation on said cylinder; and
   an extension mount for removably mounting said leg extension section to said pitch/yaw assembly, said extension mount rotatably mounted to said frame and being capable of locking said leg extension section in a given orientation relative to said extension mount.

8. The apparatus of claim 3 said frame having a first horizontal orientation relative to said base plate, moveable from said first horizontal orientation to an adjusted horizontal orientation by application of force, wherein said pitch/yaw assembly further comprises a counter wound spring coaxial with said cylinder adapted to return said frame to said first horizontal orientation upon the cessation of said force.

9. The apparatus of claim 3 wherein said extension mount comprises:
   an axle mounted within said frame; and
   a semi-circular member fixedly attached to said axle, said semi-circular member having a notch, a lip and a pressure brake portion.

10. The apparatus of claim 9 said frame having a first horizontal orientation relative to said base plate, moveable from said first horizontal orientation to an adjusted horizontal orientation by application of force, wherein said pitch/yaw assembly further comprises a locking means capable of locking said frame in a predetermined orientation on said cylinder, said locking means comprising at least two locking arms movably attached to said frame and located on opposite sides of said cylinder, said arms adapted, in one position, to compress said cylinder and lock said frame in a predetermined orientation and adapted to release said cylinder and unlock said frame otherwise.

11. The apparatus of claim 9 wherein each of said locking arms further comprises an upper portion, said semi-circular member located between said upper portions, said locking arms further adapted to lock said semi-circular member in a fixed orientation when said cylinder is compressed.

12. The apparatus of claim 1 wherein said leg extension portion comprises:
   an attachment mount, for removable attaching said distal end of said leg extension portion to said pitch/yaw assembly;
   an outer extension attached to said attachment mount;
   an inner extension slidably mounted within and extending from said outer extension; and
   an extension lock for holding said inner extension at a predetermined position within said outer extension.

13. The apparatus of claim 12 wherein said extension lock comprises:
   a collar attached to said outer extension; and
   a lever, pivotally mounted on said collar, said lever having an eccentrically mounted upper cam portion so as to cause a floating disk, freely mounted within an opening in said outer extension, to press against said inner extension when said lever is in a first position and to not cause said floating disk to press against said inner extension otherwise.

14. The apparatus of claim 12 wherein said attachment mount comprises:
   a fixed locking lip portion fixedly attached to said outer extension; and
   a movable lip portion, movably attached to said outer extension.

15. The apparatus of claim 14 wherein said movable lip portion comprises:
   a projection slidably mounted through a collar attached to said outer extension, said projection having an L-shape; and
   a spring connected to said collar and to said projection so as to bias said projection toward said fixed locking lip portion.

16. The apparatus of claim 12 wherein said means for positioning said patient's thigh is movably attached to said rail mounting bracket.

17. The apparatus of claim 1 further including a rail mounting bracket for mounting said apparatus for adjustable positioning of a patient's leg to a rail of an operating table.

18. The apparatus of claim 17 wherein said rail mounting bracket comprises:
   a rail lock for fixedly attaching said mounting bracket to said rail of said operating table;
   a rail extension; and
   a rail extension lock for fixedly attaching said rail extension to said rail lock.

19. The apparatus of claim 18 wherein said rail extension lock comprises:
   a block, said block defining a bore and having a groove on the surface of said block perpendicular to said bore; and
   a locking lever pivotally mounted in said block so as to partially obstruct said bore in one position and to leave the bore unobstructed in a second position.

* * * * *

UNITED STATES PATENT AND TRADEMARK OFFICE
CERTIFICATE OF CORRECTION

PATENT NO. : 5,056,535

DATED : October 15, 1991

INVENTOR : Leonard Bonnell

It is certified that error appears in the above-identified patent and that said Letters Patent is hereby corrected as shown below:

On the title page, In the Abstract:

Line 3, change "jaw" to --yaw--.

Signed and Sealed this

Sixth Day of April, 1993

*Attest:*

STEPHEN G. KUNIN

*Attesting Officer*     *Acting Commissioner of Patents and Trademarks*